United States Patent [19]

Dempf et al.

[11] 4,034,051

[45] July 5, 1977

[54] STABILIZATION OF PERCHLOROETHYLENE

[75] Inventors: Dominik Dempf, Mehring; Otto Fruhwirth, Burghausen; Ludwig Schmidhammer, Haiming, all of Germany

[73] Assignee: Wacker-Chemie GmbH, Munich, Germany

[22] Filed: Sept. 18, 1975

[21] Appl. No.: 614,547

[30] Foreign Application Priority Data

Oct. 18, 1974 Germany .......................... 2449667

[52] U.S. Cl. .......................................... 260/652.5 R
[51] Int. Cl.² .................. C07C 17/40; C07C 17/42
[58] Field of Search ............................. 260/652.5 R

[56] References Cited

UNITED STATES PATENTS

| | | | |
|---|---|---|---|
| 2,721,883 | 10/1955 | Stevens | 260/652.5 R |
| 2,841,625 | 7/1958 | Burch et al. | 260/652.5 R |
| 2,911,449 | 11/1959 | Herman et al. | 260/652.5 R |
| 2,935,537 | 5/1960 | Daras | 260/652.5 R |
| 2,959,623 | 11/1960 | Pray et al. | 260/652.5 R |
| 3,152,191 | 10/1964 | Cormany et al. | 260/652.5 R |

*Primary Examiner*—D. Horwitz
*Attorney, Agent, or Firm*—Hammond & Littell

[57] ABSTRACT

This invention relates to an improved stabilization of perchloroethylene by adding thereto a mixture of from 0.001% to 0.01% by weight of a possibly alkylated N-alkyl-morpholine and from 0.001% to 0.01% by weight of an alkylphenol; as well as the so-stabilized perchloroethylene.

10 Claims, No Drawings

STABILIZATION OF PERCHLOROETHYLENE

THE PRIOR ART

Chlorinated hydrocarbons tend to undergo oxidative decomposition in the presence of metals or metal salts and on exposure to heat or light. The decomposition products formed in this way can impair the quality of the chlorinated hydrocarbons and even render them useless for certain purposes.

Various methods have been proposed for stabilizing chlorinated hydrocarbons so as to hinder or prevent such decomposition. The acid components produced as a result of the decomposition can be bound by the use of acid-binding agents, for example amines, but this does not have any substantial stabilization effect (German Reichspatent No. 593,384 and German Bundespatent No. 965,397). Small amounts of phenols can be added to perchloroethylene (U.S. Pat. No. 2,008,680) to retard the oxidation, but since they are weak acids they are generally used in conjunction with amines. This, unfortunately, reduces the stabilizing effect of the phenols (German Reichspatent No. 573,105).

Combinations of phenols, saturated tertiary alcohols and, optionally, pyrrole or aniline, have been suggested for the stabilization of perchloroethylene (German Auslegeschrift No. 1,127,346), but it is often necessary to use a relatively high concentration of the pyrrole or aniline to give an adequate stabilizing effect.

Combinations of phenols, epoxides and, optionally pyrrole or aniline, have also been suggested (German Auslegeschrift No. 1,115,732), but again it is often necessary to use the aniline or pyrrole in a relatively high concentration. Morpholine has been substituted for the aniline or pyrrole in the above combination, but this has been found to exert a strongly negative influence on the stabilization effect.

Various other mixtures have been proposed for the stabilization of chlorinated hydrocarbons, such as mixtures of amines and oxiranes (U.S. Pat. No. 3,133,885), mixtures of phenols and 2-methyl-pent-3-yn-l-ol (U.S. Pat. No. 2,911,449), and mixtures of amines, primary pentanols and, optionally, phenols (Austrian Pat. No. 213,382).

The effect of the various stabilizers is often fairly specific in nature, and a stabilizer that is effective for one chlorinated hydrocarbon may not be effective for another chlorinated hydrocarbon.

OBJECTS OF THE INVENTION

An object of the present invention is to improve the stabilization of perchloroethylene and to develop an improved stable perchloroethylene.

Another object of the present invention is the development of a method for the stabilization of perchloroethylene consisting essentially of adding thereto a mixture of from about 0.001% to 0.01% by weight of at least one N-alkylmorpholine having the formula

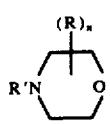

wherein R' is alkyl having from 1 to 5 carbon atoms, R is alkyl having from 1 to 5 carbon atoms and n is an integer from 0 to 3, and from about 0.001% to 0.01% by weight of at least one alkylphenol having the formula

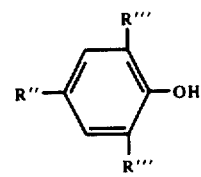

wherein R" and R''' are members selected from the group consisting of hydrogen and alkyl having from 1 to 18 carbon atoms, with the proviso that at least one of R" and R''' is alkyl having from 1 to 18 carbon atoms.

A further object of the present application is the development of a stable mixture of perchloroethylene containing a mixture of from 0.001% to 0.01% by weight of at least one N-alkylmorpholine having the formula

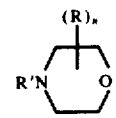

wherein R' is alkyl having from 1 to 5 carbon atoms, R is alkyl having from 1 to 5 carbon atoms and n is an integer from 0 to 3, and from about 0.001% to 0.01% by weight of at least one alkylphenol having the formula

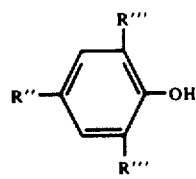

wherein R" and R''' are members selected from the group consisting of hydrogen and alkyl having from 1 to 18 carbon atoms, with the proviso that at least one of R''and R''' is alkyl having from 1 to 18 carbon atoms.

These and other objects of the present invention will become more apparent as the description thereof proceeds.

DESCRIPTION OF THE INVENTION

The present invention provides a method of stabilizing perchloroethylene, which comprises adding to the perchloroethylene a mixture of from 0.001% to 0.01% by weight, preferably from 0.04% to 0.08% by weight, of an N-alkylmorpholine and from 0.001% to 0.01% by weight, preferably from 0.04% to 0.08% by weight, of an alkylphenol.

More particularly, the present invention provides a method for the stabilization of perchloroethylene consisting essentially of adding thereto a mixture of from about 0.001% to 0.01% by weight of at least one N-alkylmorpholine having the formula

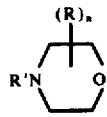

wherein R' is alkyl having from 1 to 5 carbon atoms, R is alkyl having from 1 to 5 carbon atoms and n is an integer from 0 to 3, and from about 0.001% to 0.01% by weight of at least one alkylphenol having the formula

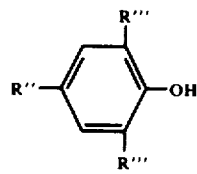

wherein R" and R''' are members selected from the group consisting of hydrogen and alkyl having from 1 to 18 carbon atoms, with the proviso that at least one of R" and R''' is alkyl having from 1 to 18 carbon atoms; as well as the stabilized perchloroethylene so produced.

Surprisingly, the addition of these fairly minimal amounts of these substances has a stabilizing effect against oxidative decomposition of the perchloroethylene. The stabilizer components dissolve in the perchloroethylene.

The alkyl chains of the N-alkylmorpholines may be either straight or branched, and the morpholine ring may be substituted in one or more of the 2,3,5 and 6 positions by further alkyl groups. Advantageously, the alkyl chains have up to 5 carbon atoms. Preferred N-alkylmorpholine are N-methylmorpholines and N-ethylmorpholines, especially those substituted by a methyl group in one or more of the 2,3,5 and 6 positions. These N-alkylmorpholines preferably have the formula

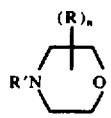

wherein R and R' are alkyl having from 1 to 5 carbon atoms and n is an integer from 0 to 3.

The alkylphenol is advantageously an o-alkylphenol, a p-alkylphenol, or an o,p-dialkylphenol, each having up to 18 carbon atoms, preferably from 2 to 8 carbon atoms, in each alkyl chain (which may be either straight or branched). Preferred alkylphenols are p-alkylphenols having a branched alkyl chain containing 3 to 5 carbon atoms, of these p-tert-butylphenol is particularly preferred. These alkylphenols preferably have the formula

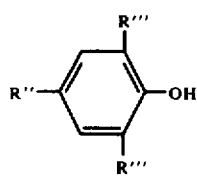

wherein R" and R''' are members selected from the group consisting of hydrogen and alkyl having from 1 to 18 carbon atoms, with the proviso that at least one of R" and R''' is alkyl having from 1 to 18 carbon atoms.

It can be advantageous to add from 0.0005% to 0.001% by weight of N-methylpyrrole, 1,3,5-cycloheptatriene, or cyclooctatetraene to the perchloroethylene in addition to the N-alkylmorpholine and the alkylphenol, so as to give an even better stabilization effect.

The stabilizing effect of the additives according to the invention is demonstrated in the following examples and comparative examples, which are demonstrative of the invention without being limitative.

EXAMPLES

The stabilization of the perchloroethylene was carried out according to the conditions of MIL test 7003.

200 ml of perchloroethylene and stabilizer were placed in a flask fitted with a reflux condenser. A steel strip measuring 12.7 × 50.8 × 1.59 mm was suspended, by means of a copper wire, in the condenser. A second steel strip, measuring 6.35 × 19.05 × 1.59 mm was placed in the liquid in the flask. A current of oxygen saturated with water was passed into the flask, through a 3 mm diameter glass tube ending 6.35 mm above the bottom of the flask, and through the liquid at a rate of about 10 to 12 bubbles per minute. The perchloroethylene was heated, and illuminated from below, by means of a 150 watt incandescent lamp bulb. The perchloroethylene was refluxed in this way for 48 hours.

The liquid was then cooled and the acidity of a sample taken therefrom, was determined in aqueous extract by titration with 0.1 N sodium hydroxide to the phenolphthalein end point.

Samples having an acid content exceeding 0.02% by weight of hydrochloric acid after the 48 hour test are considered to be ineffectively stabilized. The time taken to reach the acidity boundary of 0.02% by weight can be considered as a measure of the stabilizing effect of the additive.

The following Examples 1 to 19 use stabilizing additives according to the invention in the above test, and Comparative Examples C1 to C7 use other stabilizing additives or no additives.

| No. | ppm Stabilizer Additives | Time taken to reach acidity boundary (hours) |
|---|---|---|
| 1 | 40 N-methylmorpholine<br>40 p-tert-butylphenol | 195 |
| 2 | 40 N-methyl-2,3-dimethylmorpholine<br>40 p-tert-butylphenol | 190 |
| 3 | 40 N-methyl-2-methylmorpholine<br>40 p-tert-butylphenol | 200 |
| 4 | 80 N-methylmorpholine<br>80 p-tert-butylphenol | 230 |
| 5 | 80 N-methyl-2-methylmorpholine<br>80 p-tert-butylphenol | 220 |
| 6 | 80 N-methyl-2,3-dimethylmorpholine<br>80 p-tert-butylphenol | 225 |
| 7 | 80 N-methylmorpholine<br>80 p-tert-butylphenol<br>10 cyclooctateraene | 340 |
| 8 | 80 N-methyl-2-methylmorpholine<br>80 p-tert-butylphenol<br>10 cyclooctatetraene | 335 |
| 9 | 80 N-methyl-2,3-dimethylmorpholine<br>80 p-tert-butylphenol<br>10 cyclooctatetraene | 340 |
| 10 | 80 N-methylmorpholine<br>80 p-tert-butylphenol<br>10 N-methylpyrrole | 350 |
| 11 | 80 N-methyl-2-methylmorpholine<br>80 p-tert-butylphenol<br>10 N-methylpyrrole | 350 |
| 12 | 80 N-methyl-2,3-methylmorpholine<br>80 p-tert-butylphenol<br>10 N-methylpyrrol | 345 |
| 13 | 80 N-methylmorpholine<br>80 p-tert-butylphenol<br>10 1,3,5-cycloheptatriene | 380 |
| 14 | 80 N-methyl-2-methylmorpholine<br>80 p-tert-butylphenol<br>10 1,3,5-cycloheptatriene | 390 |
| 15 | 80 N-methyl-2,3-dimethylmorpholine | |

-continued

| No. | ppm Stabilizer Additives | Time taken to reach acidity boundary (hours) |
|---|---|---|
|  | 80 p-tert-butylphenol |  |
|  | 10 1,3,5-cycloheptatriene | 385 |
| 16 | 80 N-methylmorpholine |  |
|  | 80 o-methyl-p-tert-butylphenol |  |
|  | 10 cyclooctatetraene | 320 |
| 17 | 40 N-methyl-2-methylmorpholine |  |
|  | 40 p-isopropylphenol |  |
|  | 10 N-methylpyrrole | 260 |
| 18 | 40 N-ethyl-2,3-dimethylmorpholine |  |
|  | 40 o,o,p-trimethylphenol |  |
|  | 10 1,3,5-cycloheptatriene | 285 |
| 19 | 60 N-ethyl-2,6-dimethylmorpholine |  |
|  | 60 p-tert-butylphenol |  |
|  | 10 cyclooctatetraene | 305 |
| C1 | none | 1 |
| C2 | 80 morpholine | 36 |
| C3 | 80 N-methylmorpholine | 34 |
| C4 | 40 morpholine |  |
|  | 40 p-tert-butylphenol | 37 |
| C5 | 40 N-methylmorpholine |  |
|  | 40 epichlorhydrin | 44 |
| C6 | 80 p-tert-butylphenol | 140 |
| C7 | 40 p-tert-butylphenol |  |
|  | 40 2-methyl-pent-3-yn-1-ol | 100 |

The substantially better results obtained in Examples 1 to 19, as compared with Comparative Examples C2 to C7, show the improved stabilizing effect of the additives according to the invention.

The preceeding specific embodiments are illustrative of the practice of the invention. It is to be understood however, that other expedients known to those skilled in the art, or disclosed herein, may be employed without departing from the spirit of the invention or the scope of the appended claims.

We claim:

1. A stable mixture of perchloroethylene containing a mixture of from 0.001% to 0.01% by weight of at least one N-alkylmorpholine having the formula

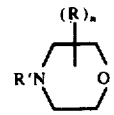

wherein R' is alkyl having from 1 to 5 carbon atoms, R is alkyl having from 1 to 5 carbon atoms and n is an integer from 0 to 3, and from about 0.001% to 0.01% by weight of at least one alkylphenol having the formula

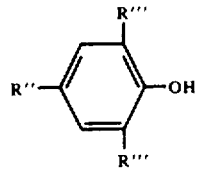

wherein R'' and R''' are members selected from the group consisting of hydrogen and alkyl having from 1 to 18 carbon atoms, with the proviso that at least one of R'' and R''' is alkyl having from 1 to 18 carbon atoms.

2. The stable mixture of claim 1 wherein from about 0.04% to 0.08% of said N-alkylmorpholine is employed.

3. The stable mixture of claim 1 wherein from about 0.04% to 0.08% by weight of said alkylphenol is employed.

4. The stable mixture of claim 1 wherein $n$ is 0.

5. The stable mixture of claim 1 wherein $n$ is 1.

6. The stable mixture of claim 1 wherein $n$ is 2.

7. The stable mixture of claim 1 wherein both R'' and R''' are alkyl having from 2 to 8 carbon atoms.

8. The stable mixture of claim 1 wherein at least one of R'' and R''' is a branched chain alkyl having from 3 to 5 carbon atoms.

9. The stable mixture of claim 1 wherein R' is selected from the group consisting of methyl and ethyl, $n$ is 0 and at least one of R'' and R''' is a branched chain alkyl having from 3 to 5 carbon atoms.

10. The stable mixture of claim 1 wherein said N-alkylmorpholine is N-methyl-2-methylmorpholine and said alkylphenol is p-tert.-butylphenol.

* * * * *